United States Patent [19]

Cioca

[11] 4,432,888

[45] Feb. 21, 1984

[54] SURFACE ACTIVE AGENTS BASED ON POLYPEPTIDES

[75] Inventor: Gheorghe Cioca, Coatesville, Pa.

[73] Assignee: Seton Company, Newark, N.J.

[21] Appl. No.: 307,016

[22] Filed: Sep. 30, 1981

[51] Int. Cl.$^3$ .................... B01F 17/30; C07C 143/34; C11D 1/88

[52] U.S. Cl. .................................. 252/354; 252/545; 252/DIG. 5; 252/DIG. 7; 252/DIG. 13; 260/501.12

[58] Field of Search ................ 252/354, 545, DIG. 7; 564/82, 84; 260/501.12

[56] References Cited

U.S. PATENT DOCUMENTS

| | | | |
|---|---|---|---|
| 2,291,634 | 8/1942 | Katzman et al. | 252/354 |
| 2,373,603 | 4/1945 | Rust et al. | 252/354 X |
| 3,948,818 | 4/1976 | Tomiyama et al. | 260/501.12 X |
| 4,279,812 | 7/1981 | Cioca | 106/124 X |
| 4,285,986 | 8/1981 | Cioca et al. | 426/657 |

OTHER PUBLICATIONS

Gustavson: "The Chemistry and Reactivity of Collagen", Academic Press Inc., New York (1956), pp. 79-81 and 196-198.

*Primary Examiner*—Richard D. Lovering
*Attorney, Agent, or Firm*—Webb, Burden, Robinson & Webb

[57] ABSTRACT

A surface active agent based upon polypeptides is disclosed. The surface active agent is comprised of the reaction product of an alkyl phenylsulfonic acid and a polypeptide at an acidic pH. The surface active agents produced in accordance with the invention are particularly useful in cosmetic applications as in shampoos and the like and in industrial applications such as in textile processing and the like.

18 Claims, No Drawings

SURFACE ACTIVE AGENTS BASED ON POLYPEPTIDES

BACKGROUND OF THE INVENTION

1. Field of the Invention

This invention relates to surface active agents and, more particularly, to surface active agents based upon polypeptides.

2. Description of the Prior Art

Surface active agents (surfactants) such as soaps, detergents and the like have broad utility in the industrial and cosmetic fields. These surface active agents form the basis, in the cosmetic field, for shampoos, hand soaps and the like. When surface active agents are used in cosmetic applications, it is necessary that they exhibit minimum dermatological irritation so as not to cause rashes, allergic reactions and the like to the user of such products.

It has been recognized that proteins are very useful in many cosmetic applications and those which are in substantially pure form have remedial effects upon skin. Thus, it has been proposed to provide surface active agents for use in shampoos and soaps which are based upon proteins. To this end, surface active agents have been proposed which are based upon polypeptides. For example, fatty acid chlorides have been reacted with protein hydrolyzates to form salts which act as surface active agents. In addition, proteins have been thermally condensed with amines in water and also condensed with alkanol amines followed by acylation with fatty acids in order to produce such surface active agents based upon proteins.

Although these prior art approaches have met with some degree of success, such approaches have the disadvantage of either having a relatively high level of skin irritation and/or being prohibitive from a cost point of view.

One particularly useful surface active agent used in shampoos and the like is dodecylbenzene sulfonic acid. This particular surface active agent has been shown to be useful as a shampoo but has the disadvantage of having a relatively high level of skin irritation.

In accordance with the present invention, a surface active agent based upon polypeptides, i.e. proteins, is provided which is low in cost, provides minimal skin and eye irritation, while providing recognized advantages which proteins have upon the skin.

BRIEF DESCRIPTION OF THE INVENTION

A surface active agent is comprised of the reaction product of an alkyl phenylsulfonic acid and a polypeptide. The surface active agents of the present invention are useful in both cosmetic and industrial applications.

DETAILED DESCRIPTION OF THE INVENTION

The alkyl phenylsulfonic acids useful in the practice of the invention are those which have a sulfonate ($SO_3$ group) attached to a benzene ring and also have a hydrophobic or oleophilic group also attached to the benzene ring. Preferably the hydrophobic group is an alkyl group having up to 25 carbon atoms. Most preferably the alkyl group is a straight chain alkyl group in order to provide maximum solubilization of oils, fats and the like via this hydrophobic moiety. Most preferably the alkyl group has up to 12 carbon atoms and one particularly useful alkyl phenylsulfonic acid is dodecylbenzene sulfonic acid.

Polypeptides useful in the practice of the invention are preferably those polypeptides derived from animal hide and tendons and, most preferably, polypeptides which are derived from bovine hides and tendons. More particularly, these polypeptides are derived from collagen and/or elastin.

"Natural insoluble collagen", as used herein, means and refers to collagen which cannot be dissolved in an aqueous alkaline or in an inorganic salt solution without chemical modification and includes hides, splits and other mammillian or reptilian coverings. More particularly, "natural insoluble collagen" means and refers to the corium which is the intermediate layer of a bovine hide between the grain and flesh sides.

Collagen constitutes the connective tissue and is the major type of fibrous protein in higher vertebrae. Collagen in its natural state exists in a triple chain helix along with a constant periodicity between aligned triple chains. The triple helical configuration of collagen is sometimes referred to as a fibril and the fibrils align with an axial periodicity of about 640Å.

Although there are several types of collagen, the major type is referred to as type I which is the major collagen of skin, bones and tendons. Type I collagen has a chain composition of $[\alpha I(I)_2 \alpha 2]$. The $\alpha I(I)$ and $\alpha 2$ chains are homologous. This natural insoluble collagen can be processed in many ways to sever collagen chains into oligopeptides. These oligopeptides have been found to be particularly useful in the cosmetic field when they are in substantially pure form. The oligopeptides in substantially pure form are particularly useful polypeptides in preparing the surface active agents in accordance with the invention.

A process for preparing oligopeptides which are polypeptides useful in the practice of the invention, is disclosed in U.S. Pat. No. 4,285,986, incorporated herein by reference and made a part hereof.

These oligopeptides have a molecular weight between about 5000 and 20,000 and, in accordance with the practice of the invention, it is preferred that such molecular weight parameters for the polypeptides be observed when the surface active agent is to be used in cosmetic applications.

In addition, polypeptides useful in the practice of the invention can be those which are derived from elastin. These polypeptides which are derived from elastin have a molecular weight of about 800 and are water and alcohol soluble. In order to solubilize the elastin, it is necessary to hydrolyze it in order to reduce its molecular weight and eliminate crosslinkages. Such partially hydrolyzed elastin can be obtained from the process disclosed in U.S. patent application Ser. No. 296,985, filed Aug. 27, 1981, now U.S. Pat. No. 4,363,760, entitled "Partially Hydrolyzed Elastin From Limed Hide Trimmings" by Gheorghe Cioca. This patent application is incorporated herein by reference and made a part hereof. These polypeptides, which are derived from elastin, are also particularly useful in preparing the surface active agents in accordance with the invention for use in cosmetic applications.

Where the surface active agents are to be used in industrial applications thereby not requiring extremely low skin irritation, polypeptides such as bone glues, gelatins and similar materials may be used to form the surface active agents. However, it is desirable that the polypeptides useful in the practice of the invention be those which are water soluble, in order to provide a substantially hydrophilic moiety to the surface active agent in conjunction with the hydrophobic moiety provided by the alkyl phenyl group. The polypeptide can have a molecular weight up to 100,000.

In preparing the surface active agents in accordance with the practice of the invention, 1 to 1.5 parts by weight of the sulfonic acid to 0.9 to 1.65 parts by weight of the polypeptide are used. More preferably, a ratio of 1 to 1.2:1 to 1.4 of sulfonic acid:polypeptide is observed.

It has been found that the most desirable surface active agents are produced by reacting the alkyl phenylsulfonic acid and polypeptide in the presence of either a peroxide or alcohol or a combination thereof. When a peroxide is used in synthesizing the surface active agent, it is used at a level of up to about 5 percent by weight based upon the weight of the polypeptide and, more preferably, at a level of about 3 percent by weight based upon the weight of the polypeptide. The peroxides useful in the practice of the invention are both inorganic and organic peroxides while the inorganic peroxides are preferred. Exemplary inorganic peroxides are hydrogen peroxide and ammonium persulfate. Organic peroxides may be used and are selected on the basis of decomposition half-life in the presence or absence of a suitable accelerator. Typical organic peroxides are tertiary-butyl hydroperoxide, benzol peroxide, lauryl peroxide, dicumene hydroperoxide and the like. Combinations of various peroxides may be used in producing the surface active agent. It has been found that hydrogen peroxide and ammonium persulfate mixed together in approximately equal quantities are particularly useful in forming the surface active agent in accordance with the invention. It is not known the exact effect which the peroxide has upon the reaction of the alkyl phenylsulfonic acid and the polypeptide. However, it is known that a clear, nonskin irritating surface active agent is produced when such peroxides are used.

Nonskin irritating surface active agents can also be prepared by performing the reaction between the alkyl phenylsulfonic acid and the polypeptide in the presence of a lower alcohol, i.e. three carbon alcohols or less. In particular, ethyl alcohol has been found to be particularly useful in preparing the surface active agents. When preparing surface active agents in accordance with the invention in the presence of an alcohol, about 60 to 80 percent by weight alcohol based upon the weight of polypeptides is utilized.

The surface active agents in accordance with the invention are prepared by charging to a suitable vessel the alkyl phenylsulfonic acid and the polypeptide. Water is added to form a solution of 60 to 75 percent by weight solids. The peroxide is charged to the mixture and the mixture is heated at 55° C. to 85° C. and, more preferably, 60° C. to 75° C. for 2 to 4 hours and, more preferably, 3 to 3.5 hours. After the reaction has been conducted, the surface active agent is then neutralized with the base to a pH of 6 to 8 and, more preferably, to a pH of 7. Any known base can be utilized for neutralization. The organic bases such as amines and the like and the inorganic bases such as the alkali hydroxides, alkali earth metal hydroxides can be utilized. However, it is preferred that sodium hydroxide or ammonium hydroxide be used for purposes of neutralization. More particularly preferred, especially in the area of shampoos and skin soaps are tertiary amines and, most preferably, triethanol amine. When the surface active agent in accordance with the invention is prepared in the presence of an alcohol, the alkyl phenylsulfonic acid and the polypeptide are charged to a suitable vessel along with sufficient water to form a 40 to 50 percent solid solution. The product is then heated and neutralized as previously described.

One particular advantage of the surface active agents useful in the practice of the invention is that they are amphoteric. This amphoteric nature is attributable to the sulfonate group in combination with the amino groups in the polypeptides. Thus, either anionic or cationic surface active agents can be prepared based upon ions present in the particular media.

The following examples will more fully illustrate the preparation of the surface active agents in accordance with the invention.

EXAMPLE I

In a suitable vessel was charged 5 liters of dodecylbenzene sulfonic acid and 15 liters of 35 percent by weight hydrolyzed collagen in water having a molecular weight of up to 20,000 and prepared in accordance with Example I of U.S. Pat. No. 4,285,986, previously cited herein. 1.5 percent by weight of 70 percent hydrogen peroxide and 1.5 percent by weight of ammonium persulfate, both based upon the weight of hydrolyzed collagen, were charged to the vessel. The ingredients were agitated until homogenous and heated at 75° C. for 2 hours.

The reaction product was cooled to room temperature and neutralized with sodium hydroxide to a pH of 7. The neutralized surface active agent had a solids concentration of 41.65 percent total weight solids, 6.69 percent ash and 21.1 percent protein.

EXAMPLE II

Example I was repeated except that the reaction product was neutralized to a pH of 7 with ammonium hydroxide. This product had 43.15 percent total weight solids, 0.55 percent ash and 23.18 percent protein.

EXAMPLE III

Example I was repeated except that the reaction product was neutralized with triethanolamine to a pH of 7. This product had a total weight solids of 59.58 percent, 0.364 percent ash and 32.66 percent protein.

The surface active agent prepared in accordance with Example III is particularly useful in cosmetic applications as demonstrated by a primary skin irritation index of 0.12 which is extremely low. Typical primary skin irritation indicies for cosmetics is normally in the range of 1 to 2 and the sodium salt of dodecylbenzene sulfonic acid is about 4.5.

When the surface active agent is incorporated into a shampoo or skin soap, other constituents can be added. More particularly, proteins such as the oligopeptides described in U.S. Pat. No. 4,285,986 or biologically active collagen, as is described in U.S. Pat. No. 4,279,812, may be used to impart remedial effects upon the skin and hair. The following example is illustrative of such a composition.

EXAMPLE IV

Two grams of the surface active agent prepared in accordance with Example III was mixed with 28 milliliters of 1 percent by weight biologically active collagen prepared in accordance with Example I of U.S. Pat. No. 4,279,812. The homogenous solution was freeze dried by freezing at −50° C. for three hours and then applying a vacuum of 10 microns mercury for 12 hours until the composite reached the temperature of 30° C. A foam-like material was produced which was useful as a soap or a shampoo having good cleaning and dermatological properties.

As is well recognized by those skilled in the art, many other materials may be incorporated along with the surface active agent to provide formulations useful as shampoos, skin and face soaps and the like. Further, materials may be added which are particularly useful for cleaning textiles and similar materials.

Although the invention has been described with reference to particular processes and particular ingredients, the invention is only to be limited so far as is set forth in the accompanying claims.

I claim:

1. A surface active agent comprised of the reaction product of an alkyl phenylsulfonic acid and a polypeptide at an acidic pH at a ratio of 1 to 1.5 parts by weight of said sulfonic acid to 0.9 to 1.65 parts by weight of said polypeptide.

2. The surface active agent of claim 1 wherein the alkyl group on said sulfonic acid has up to 25 carbon atoms.

3. The surface active agent of claim 2 wherein said alkyl group has 12 carbon atoms.

4. The surface active agent of claim 3 wherein said alkyl phenylsulfonic acid is dodecylbenzene sulfonic acid.

5. The surface active agent of claim 1 wherein said reaction product is produced in the presence of a peroxide.

6. The surface active agent of claim 5 wherein said peroxide is ammonium persulfate.

7. The surface active agent of claim 5 wherein said peroxide is hydrogen peroxide.

8. The surface active agent of claim 5 wherein said peroxide is present at a level of up to 5 percent by weight based upon the weight of polypeptide.

9. The surface active agent of claim 1 wherein said polypeptide has a molecular weight of up to 100,000.

10. The surface active agent of claim 9 wherein said polypeptide has a molecular weight of up to 20,000.

11. The surface active agent of claim 10 wherein said polypeptides are oligopeptides derived from collagen.

12. The surface active agent of claim 10 wherein said polypeptides are oligopeptides derived from elastin.

13. The surface active agent of claim 1 having a pH of about 7.

14. The surface active agent of claim 13 having been neutralized with a base selected from the group consisting of a tertiary amine and an inorganic base.

15. The surface active agent of claim 14 wherein said tertiary amine is triethanolamine.

16. The surface active agent of claim 1 in combination with biologically active collagen.

17. The combination of claim 16 wherein said biologically active collagen is present at a level of up to 1 percent by weight.

18. The combination of claim 16 which is freeze dried.

* * * * *